(12) United States Patent
Hijikata et al.

(10) Patent No.: US 9,249,394 B2
(45) Date of Patent: Feb. 2, 2016

(54) METHOD FOR PRODUCING EPITHELIAL STEM CELLS

(75) Inventors: Makoto Hijikata, Kyoto (JP); Hassan Hussein Aly, Kyoto (JP); Tatsuya Yamaguchi, Tsuruga (JP)

(73) Assignees: KYOTO UNIVERSITY, Kyoto-shi (JP); TOYOBO CO., LTD., Osaka-shi (JP)

( * ) Notice: Subject to any disclaimer, the term of this patent is extended or adjusted under 35 U.S.C. 154(b) by 0 days.

(21) Appl. No.: 14/007,133

(22) PCT Filed: Mar. 23, 2012

(86) PCT No.: PCT/JP2012/057468
§ 371 (c)(1),
(2), (4) Date: Sep. 24, 2013

(87) PCT Pub. No.: WO2012/133156
PCT Pub. Date: Oct. 4, 2012

(65) Prior Publication Data
US 2014/0030809 A1 Jan. 30, 2014

(30) Foreign Application Priority Data
Mar. 25, 2011 (JP) ................................. 2011-067112

(51) Int. Cl.
C12N 5/00 (2006.01)
C12N 5/071 (2010.01)
C12N 9/12 (2006.01)
A61K 35/36 (2015.01)

(52) U.S. Cl.
CPC .............. *C12N 5/0672* (2013.01); *C12N 5/067* (2013.01); *C12N 9/12* (2013.01); *C12Y 207/11022* (2013.01); *A61K 35/36* (2013.01); *C07K 2319/43* (2013.01); *C12N 2500/90* (2013.01); *C12N 2501/119* (2013.01); *C12N 2501/12* (2013.01); *C12N 2501/155* (2013.01); *C12N 2501/405* (2013.01); *C12N 2510/00* (2013.01); *C12N 2533/30* (2013.01); *C12N 2533/54* (2013.01)

(58) Field of Classification Search
None
See application file for complete search history.

(56) References Cited

U.S. PATENT DOCUMENTS 7,601,534 B1 10/2009 Hatzfeld et al.
2009/0325289 A1 12/2009 Hatzfeld et al.

FOREIGN PATENT DOCUMENTS

| JP | 2002-512788 A | 5/2002 |
|---|---|---|
| JP | 2003-501081 A | 1/2003 |
| JP | 2009-520474 A | 5/2009 |
| WO | 99/55844 A2 | 11/1999 |
| WO | 2007/071339 A1 | 6/2007 |

OTHER PUBLICATIONS

Ramirez et al., Oncogene 2003, 22(3)433-44.*
Chiba, Tetsuhiro et al., "Enhanced Self-Renewal Capability in Hepatic Stem/Progenitor Cells Drives Cancer Initiation", Gastroenterology, 2007, vol. 133, No. 3, pp. 937-950, cited in ISR.
Chiba, Tetsuhiro et al., "Bmi1 Promotes Hepatic Stem Cell Expansion and Tumorigenicity in Both Ink4a/Arf-Dependent and -Independent Manners in Mice", Hepatology, 2010, vol. 52, No. 3, pp. 1111-1123, cited in ISR.
Kamiya, Akihide et al., "Prospero-Related Homeobox 1 and Liver Receptor Homolog 1 Coordinately Regulate Long-Term Proliferation of Murine Fetal Hepatoblasts", Hepatology, 2008, vol. 48, No. 1, pp. 252-264, cited in ISR.
Lange, Christian et al., "Cdk4/CyclinD1 Overexpression in Neural Stem Cells Shortens G1, Delays Neurogenesis, and Promotes the Generation and Expansion of Basal Progenitors", Cell Stem Cell, 2009, vol. 5, pp. 320-331, cited in ISR.
Alison, Malcolm R., et al., "Application of liver stem cells for cell therapy", Seminars in Cell & Developmental Biology, 2007, vol. 18, pp. 819-826, cited in ISR.
Ramirez, Ruben D., et al., "Immortalization of Human Bronchial Epithelial Cells in the Absence of Viral Oncoproteins", Cancer Research, 2004, vol. 64, pp. 9027-9034, cited in specification.
International Search Report of PCT/JP2012/057468, mailing date of Jun. 19, 2012.
Gaelle Del Castillo et al., "Isolation and Characterization of a Putative Liver Progenitor Population After Treatment of Fetal Rat Hepatocytes With TGF-Beta", Journal of Cellular Physiology, Jun. 1, 2008, vol. 215, No. 3, pp. 846-855; cited in Extended European Search Report dated Nov. 19, 2014 (10 pages).
Extended European Search Report dated Nov. 19, 2014, issued in corresponding EP Application No. 12765426.7 (7 pages).

* cited by examiner

*Primary Examiner* — Doug Schultz
(74) *Attorney, Agent, or Firm* — Westerman, Hattori, Daniels & Adrian, LLP

(57) ABSTRACT

An object of this invention is to provide a method, etc., for efficiently proliferating a pluripotent epithelial somatic stem cell. A method for producing an epithelial somatic stem cell comprising Steps (A) and (B) below:
(A) expressing a gene of a protein having an activity for causing a cell in G0 phase or G1 phase to enter S phase, in a cell population including an epithelial somatic stem cell; and
(B) culturing the cell obtained in Step (A) in the presence of an extracellular growth factor.

7 Claims, 7 Drawing Sheets

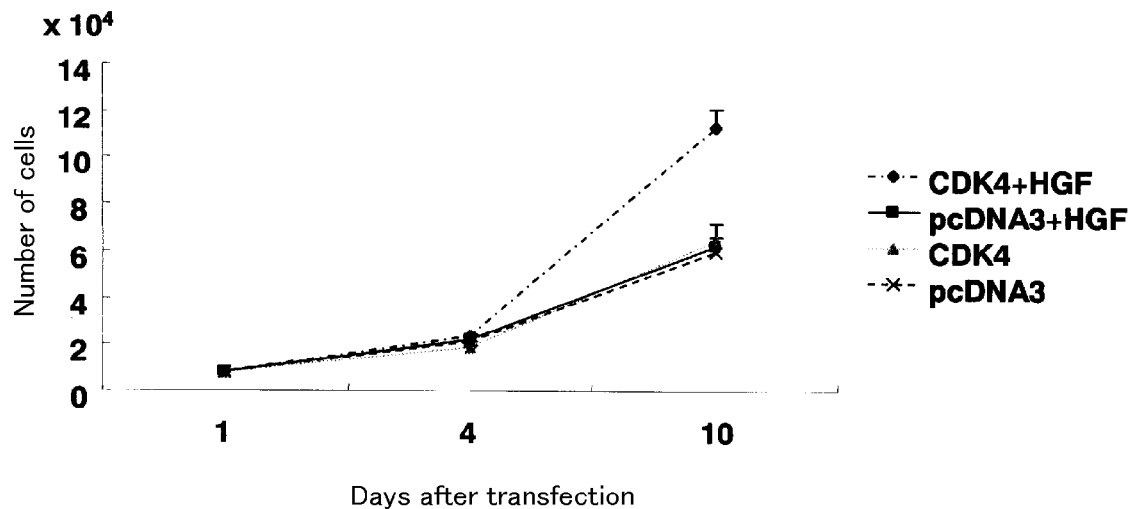

Fig. 3
|  | Albumin | CYP1B1 | CYP2B | CYP2C9 | CYP2E1 | CYP3A4 |
|---|---|---|---|---|---|---|
| original | - | + | -/+ | - | + | + |
| 1 month | + | + | + | + | - | + + |
| 2 month | + + | + | -/+ | + | -/+ | + |
Fig. 4
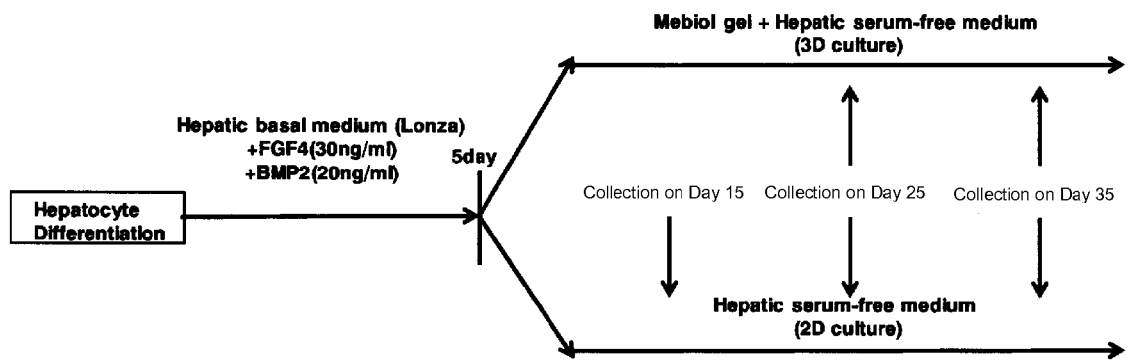
Fig. 5
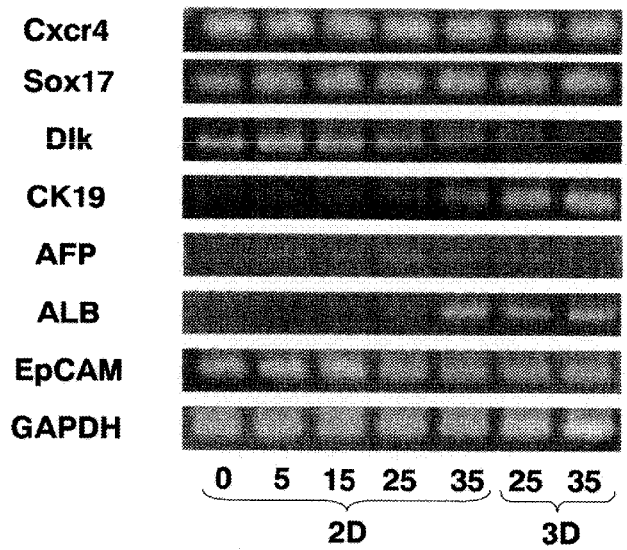

| Cell type marker No. | Albumin hepatic parenchymal cells | AFP hepatic stem cells/ hepatoblasts | c-Met HGF receptor | EpCam hepatoblasts | Dlk hepatic stem cells/bile duct cells | CK19 hepatic stem cells/bile duct cells | Thy1 mesenchymal stem cells | c-kit hemopoietic stem cell | CD34 hemopoietic precusor cell |
|---|---|---|---|---|---|---|---|---|---|
| 1,4,5,6 | - | + | + | + | + | + | + | + | - |
| 2,3 | - | -/+ | + | + | + | + | + | + | - |

```
                        SEQUENCE LISTING

<160> NUMBER OF SEQ ID NOS: 4

<210> SEQ ID NO 1
<211> LENGTH: 60
<212> TYPE: DNA
<213> ORGANISM: Artificial sequence
<220> FEATURE:
<223> OTHER INFORMATION: Primer

<400> SEQUENCE: 1
agagggaatt caccatggat tacaaggatg acgatgacaa gatggctacc tctcgatatg         60

<210> SEQ ID NO 2
<211> LENGTH: 33
<212> TYPE: DNA
<213> ORGANISM: Artificial sequence
<220> FEATURE:
<223> OTHER INFORMATION: Primer

<400> SEQUENCE: 2
ctctctctag atcactccgg attaccttca tcc                                      33

<210> SEQ ID NO 3
<211> LENGTH: 55
<212> TYPE: DNA
<213> ORGANISM: Artificial sequece
<220> FEATURE:
<223> OTHER INFORMATION: Primer

<400> SEQUENCE: 3
aagcttacca tggattacaa ggatgacgac gataaggaga aggacggcct gtgcc              55

<210> SEQ ID NO 4
<211> LENGTH: 28
<212> TYPE: DNA
<213> ORGANISM: Artificial sequence
<220> FEATURE:
<223> OTHER INFORMATION: Primer

<400> SEQUENCE: 4
ggatcctcag gctgtattca gctccgag                                            28
```

METHOD FOR PRODUCING EPITHELIAL STEM CELLS

TECHNICAL FIELD

The present invention relates to a method for producing epithelial somatic stem cells, and applied technologies thereof.

BACKGROUND ART

The use of cells, in particular, human cells, is now indispensable in disease research or new drug development. The demand therefor is expected to further increase in the future.

The cells are generally prepared by isolating them from tissues obtained from a biological organism, and are cultured to be used for various experiments and research. In such usage, differentiated cells are often used according to the target usage. However, the proliferation of differentiated cells ex vivo may be difficult. Moreover, differentiated cells have many problems, such as the rapid loss of original activity, considerable production cost, and great characteristic variation depending on the donor. For example, human hepatic cells are known for their variation in drug-metabolizing enzyme activity or drug-transporting activity. Further, hepatic cells obtained from biological tissue suffer a problematic rapid loss of function after culture.

To solve the above problems, in particular, the problem regarding cell proliferation ability, differentiated cells are often immortalized. For example, various methods for cell immortalization, including a method for introducing a SV (simian virus) 40 large T-antigen gene or a human telomerase gene into human hepatic cells, have been attempted (Non-patent Document 1). However, most immortalized cells lose their original differentiation character. There have been no reports of an immortalized cell fully exhibiting its original function. For example, telomerase genes are hardly expressed in normal cells of a human tissue. Further, using cancer genes for the production of immortalized cells is not regarded as desirable, considering the possibility of their deviation from the normal cells.

On the other hand, a method of isolating somatic stem cells having high proliferative ability from a biological tissue, and culturing and proliferating the cells ex vivo has been known as a means for obtaining a large number of normal primary cultured cells. Acquisition of somatic stem cells may be performed, for example, by a method for obtaining somatic cells from a biological tissue, and isolating somatic stem cells using a cell sorter according to the expression pattern of the cell-surface molecules. However, it is difficult to obtain a tissue containing desired somatic stem cells and select a suitable antibody for the somatic stem cells, and it is not easy to obtain a somatic stem cell population having high purity. Further, since the number of stem cells in a tissue is very small, a large number of cells (for example, $10^8$ or more cells) is necessary as a starting material for the collection of a certain number of stem cells using a cell sorter. Moreover, even if a somatic stem cell population having high purity can be obtained, it is difficult to proliferate the cells by culture (in particular, it is difficult to culture the cells while maintaining the original properties of the somatic stem cells).

A method for proliferating pluripotent stem cells such as ES cells or iPS cells, and inducing differentiation of the proliferated cells to obtain the desired differentiated cells, has also been known. Although some reports confirmed differentiation of a part of ES cells or iPS cells, their differentiation efficiencies are insufficient at present, and various other cells are often contained. Thus the isolation of a highly pure differentiated cell population remains an arduous task.

Under such circumstances, there has been a strong need for a method for stably supplying a highly pure somatic stem cell population having a certain differentiation ability.

CITATION LIST

Patent Documents

Patent Document 1: JP2002-512788A
Patent Document 2: JP2003-501081A
Patent Document 3: JP2009-520474A

Non-Patent Documents

[Non-patent Document 1] Ramirez, D. R. et al., Cancer Research 64, 9027-9034, 2004

SUMMARY OF INVENTION

Technical Problem

An object of the present invention is to solve the above problems of hitherto-known techniques. More specifically, so as to create a system for supplying highly pure epithelial differentiated cells having a normal property, an object of the present invention is to provide epithelial somatic stem cells capable of proliferation with their pluripotencies; and a method for proliferating epithelial somatic stem cells with their pluripotencies, and the like.

Solution to Problem

The inventors of the present invention conducted extensive research to solve the above problems, and found that by introducing a gene of a protein that has an activity for causing cells in G0 phase or G1 phase to enter S phase, into a cell population including epithelial somatic stem cells, and culturing the cell population in the presence of an extracellular growth factor, only epithelial somatic stem cells can be predominantly proliferated without introducing other genes; and proliferated epithelial somatic stem cells can be easily, efficiently, and exclusively acquired. Further, the inventors of the present invention confirmed that the epithelial somatic stem cells thus obtained can be differentiated into desired specific cells by culturing the cells in a culture medium suitable for differentiation (more specifically, the inventors confirmed that the aforementioned epithelial somatic stem cells have pluripotency). The inventors of the present invention conducted further intensive research, and found that the differentiation of the pluripotent epithelial somatic stem cells can be promoted by culturing the cells in a three-dimensional culture medium. With further analysis and improvement based on the above findings, the inventors completed the present invention.

The present invention is summarized below.
I. Method for Producing Epithelial Somatic Stem Cell
I-1. A method for producing an epithelial somatic stem cell comprising Steps (A) and (B) below:
(A) expressing a gene of a protein having an activity for causing a cell in G0 phase or G1 phase to enter S phase, in a cell population comprising an epithelial somatic stem cell.
(B) culturing the cell obtained in Step (A) in the presence of an extracellular growth factor.

I-2. The method according to I-1, wherein the expression is transient expression.

I-3. The method according to I-1 or I-2, wherein Step (A) and Step (B) are repeated at least twice.

I-4. The method according to any one of I-1 to I-3, wherein the protein is a cyclin-dependent kinase.

I-5. The method according to any one of I-1 to I-4, wherein the protein is at least one protein selected from the group consisting of cyclin-dependent kinase 4 and cyclin-dependent kinase 6.

I-6. The method according to any one of I-1 to I-5, wherein the cell population is a primary-cultured somatic cell population.

I-7. The method according to any one of I-1 to I-6, wherein the cell population is a hepatic cell population.

I-8. The method according to I-7, wherein the extracellular growth factor is a hepatocyte growth factor (HGF).

I-9. The method according to any one of I-1 to I-8, wherein epithelial somatic stem cells constitutes 50% or more of the produced cell population.

I-10. The method according to any one of I-1 to I-8, wherein the cell population substantially consisting only of epithelial somatic stem cell is obtained.

I-11. The method according to any one of I-1 to I-8, wherein an isolated epithelial somatic stem cell population is obtained.

II. Epithelial Somatic Stem Cell

II-1. An epithelial somatic stem cell obtained by the method according to any one of I-1 to I-11.

II-2. The epithelial somatic stem cell according to II-1, wherein the epithelial somatic stem cell is albumin negative, c-Met positive, EpCAM positive, Dlk positive, Thy1 positive, CK19 positive, and CD34 negative.

II-3. The epithelial somatic stem cell according to II-1 or II-2, wherein an exogenous gene has been further introduced thereto.

III. Method for Producing Epithelial Differentiated Cell

III-1. A method for producing an epithelial differentiated cell, comprising the step of differentiating the epithelial somatic stem cell according to any one of II-1 to II-3.

III-2. The method according to III-1, wherein the differentiation step comprises the step of performing three-dimensional culture.

III-3. The method according to III-1, wherein the differentiation step comprises the step of performing culture in a substantially serum-free culture medium.

III-4. The method according to III-3, wherein the substantially serum-free culture medium is a culture medium that substantially does not contain an epithelial growth factor and/or a liver cell growth factor.

IV. Epithelial Differentiated Cell

IV-1. An epithelial differentiated cell obtainable by the method according to any one of III-1 to III-4.

V. Pharmaceutical Composition

V-1. A pharmaceutical composition comprising the epithelial somatic stem cell according to any one of II-1 to 11-3, or the epithelial differentiated cell according to IV-1, as an active ingredient.

VI. Kit for Isolating Epithelial Somatic Stem Cell

VI-1. A kit for isolating an epithelial somatic stem cell from a cell population comprising epithelial somatic stem cells, the kit comprising an expression vector for expressing a protein having an activity for causing a cell in G0 phase or G1 phase to enter S phase; and an extracellular growth factor.

VII. Method for Producing Epithelial Somatic Stem Cell with Reactivated Cell Cycle VII-1. A method for producing an epithelial somatic stem cell with reactivated cell cycle, comprising the step of:
expressing a gene of a protein having an activity for causing a cell in G0 phase or G1 phase to enter S phase in an epithelial somatic stem cell that has left a cell cycle.

Advantageous Effects of Invention

The method of the present invention is capable of predominantly proliferating epithelial somatic stem cells in a mixed cell population, even when the cell population contains a very small amount of epithelial somatic stem cells. Accordingly, the method of the present invention enables efficient production of highly pure epithelial somatic stem cells, compared with the hitherto-known method for isolating somatic stem cells using a cell sorter or the like. The present invention is capable of efficiently obtaining stem cells from a relatively small cell population (for example, a cell population of about $10^5$ to $10^6$ cells). Thus, in the present invention, it is not necessary to prepare a large number of cells, as in the method using a cell sorter. Moreover, since the epithelial somatic stem cells produced through the method of the present invention have pluripotency, they can be differentiated into desired differentiated cells according to need.

In the present invention, the gene to be introduced to proliferate epithelial stem cells can be transiently expressed. Therefore, the epithelial somatic stem cells produced through the method of the present invention do not contain an exogenous gene, and thereby have substantially the same property and structure as those of epithelial stem cells that proliferate in vivo. Hence the present invention stably supplies epithelial somatic stem cells having properties identical or very similar to those of the epithelial somatic stem cells that proliferate in vivo; epithelial differentiated cells having properties identical or very similar to those of epithelial differentiated cells that differentiate in vivo; a cell group of these cells; and a model tissue. The thus-obtained epithelial stem cells and epithelial differentiated cells are superior in safety, and thus can be used in various research and development such as new drug development, disease research, and the like.

The epithelial stem cells and epithelial differentiated cells produced through the method of the present invention also serve as host cells for expressing exogenous genes, and thus can also be used as a medicine for gene therapy by introducing a gene for treating a disease epithelial tissue into the epithelial stem cells or epithelial differentiated cells.

BRIEF DESCRIPTION OF DRAWINGS

FIG. 1 is a graph showing the influence of introduction of CDK4 expression plasmid and addition of HGF on the cell proliferative ability of a human hepatic cell population.

FIG. 2 shows the results of property analysis of HYM cells in Example 2.

FIG. 3 shows the results of property change caused by induction of differentiation of HYM cells in Example 3.

FIG. 4 shows the procedure of an experiment of differentiation induction of HYM cells in Example 4.

FIG. 5 shows the results of expression of a differentiation marker gene in HYM cells in Example 4. The numbers in the horizontal axis denote the number of days after the priming culture.

FIG. 14 shows changes in cell form due to induction of differentiation of G-HYM cells using a growth factor-deficient serum-free culture medium in Example 7. The upper-left image shows the results of culture using a hepatic cell serum-free culture medium containing EGF. The upper-right image shows the results of culture using a hepatic cell serum-free culture medium that does not contain EGF. The lower-left image shows the results of culture using a hepatic cell serum-free culture medium that does not contain LCGF. The lower-right image shows the results of culture using a hepatic cell serum-free culture medium that does not contain EGF and LCGF.

FIG. 15 shows the results of property analysis of HYM cells in Example 8.

DESCRIPTION OF EMBODIMENTS

Figure 6:
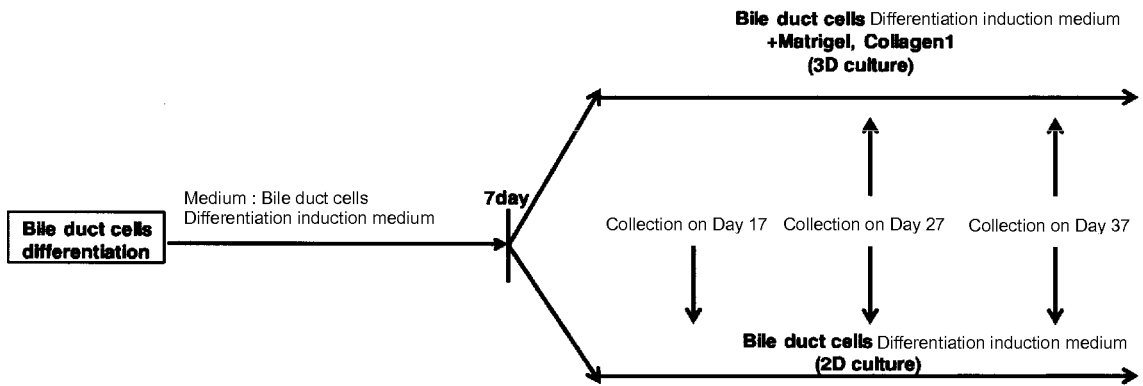
FIG. 6 shows the procedure of an experiment of differentiation induction of HYM cells in Example 5.

Specific embodiments of the present invention are described below.

A. Production Method for Epithelial Somatic Stem Cells

The production method for an epithelial somatic stem cell according to the present invention has the following Steps (A) and (B):

Step (A) of expressing a gene of a protein having an activity for causing cells in G0 phase or G1 phase to enter S phase in a cell population comprising epithelial somatic stem cells; and Step (B) of culturing the cell obtained in Step (A) in the presence of an extracellular growth factor.

1. Step (A)

Step (A) is to express a gene of a protein having an activity for causing cells in G0 phase or G1 phase to enter S phase in a cell population comprising epithelial somatic stem cells.

(1) Epithelial Somatic Stem Cells

Epithelial somatic stem cells refer to somatic stem cells obtained from a tissue containing epithelial cells. Epithelial cells refer to cells that form surfaces of epithelial tissues for covering free surfaces inside and outside the body. Epithelial cells include cells constituting an ectodermal epithelium, cells constituting a mesodermal epithelium, and cells constituting an endodermal epithelium. Examples of epithelial cells include, but are not limited to, epidermis cells constituting epidermis covering the body surface; narrowly defined epithelial cells constituting epithelium constituting mucosa of a hollow organ such as alimentary tract or respiratory tract; acinar cells constituting exocrine gland; glandular cells constituting endocrine gland; and cells from parenchymatous organs with a secretion or absorption function, such as hepatic cells or tubular epithelium.

Further, epithelial differentiated cells refer to cells resulting from differentiation of epithelial somatic stem cells.

In Step (A), the epithelial somatic stem cells in which a gene encoding a protein having an activity for causing the cells in G0 phase or G1 phase to enter S phase is to be expressed may be isolated epithelial somatic stem cells, a cell population comprising multiple epithelial somatic stem cells, or a cell population comprising epithelial somatic stem cells and other cells (hereinafter these cell populations are collectively called "a cell population comprising epithelial somatic stem cells").

(2) Cell Population Comprising Epithelial Somatic Stem Cells

The "cell population comprising epithelial somatic stem cells" used as the starting material is not particularly limited, insofar as it includes epithelial somatic stem cells. The proportion of epithelial somatic stem cells in the cell population is not particularly limited. For example, it is sufficient if the cell population include epithelial somatic stem cells at a proportion of $1/100000$ to $1/1000$. The cell population comprising epithelial somatic stem cells may be, for example, primary cultured cells, or subcultured cells (in the present specification, these cells may be referred to as "early-passage cultured cells") resulting from repeated subculture of cells to the extent in which the original function of the cells in vivo can be maintained, after the cells are isolated from a living organism. The number of subcultures of the early-passage cultured cells is preferably not more than 10, more preferably not more than 5, further preferably not more than 2.

Some primary cultured cells, such as primary cultured hepatic cells, are incapable or nearly incapable of subculture. However, even for such cells, the cells can adhere to the culture medium in some cases and exhibit the original function only for a certain period of time. Thus, when such cells are used as the material, it is preferable to select cells that adhere to the culture medium and exhibit the original function.

The organs/tissues for obtaining the cell population comprising epithelial somatic stem cells are not particularly limited, and are selected depending on the intended use of the ultimately obtained epithelial somatic stem cells or epithelial differentiated cells. Examples of the organs/tissues include pancreas, liver, kidney, skin, follicle, cornea, intestinal tract, mucosa of the bladder, oral mucosa, and the like. Particularly preferred organs/tissues are liver, skin, and intestinal tract.

The living organisms for obtaining the cell population comprising epithelial somatic stem cells are appropriately selected according to the intended use of epithelial somatic stem cells or epithelial differentiated cells. Examples of living organisms include mammals such as mice, rat, guinea pig, hamster, rabbit, feline, canine, sheep, swine, bovine, goat, ape, human, and the like. When the obtained epithelial somatic stem cells or epithelial differentiated cells are used for the research or treatment of human disease (for example, liver disease), it is preferable to use human cells.

When a pancreatic cell population is used as the cell population comprising epithelial somatic stem cells, pancreatic stem cells, etc., may be obtained through the production method of the present invention.

When a hepatic cell population is used as the cell population comprising epithelial somatic stem cells, hepatic stem cells, etc., may be obtained through the production method of the present invention.

When a renal cell population is used as the cell population comprising epithelial somatic stem cells, renal tubular epithelium stem cells, etc., may be obtained through the production method of the present invention.

When a skin cell population is used as the cell population comprising epithelial somatic stem cells, epidermis stem cells, etc., may be obtained through the production method of the present invention.

When a follicular cell population is used as the cell population comprising epithelial somatic stem cells, follicular stem cells, etc., may be obtained through the production method of the present invention.

When a corneal cell population is used as the cell population comprising epithelial somatic stem cells, corneal epithelial stem cells, etc., may be obtained through the production method of the present invention.

When an intestinal cell population is used as the cell population comprising epithelial somatic stem cells, intestinal epithelial stem cells, etc., may be obtained through the production method of the present invention.

The cell population comprising epithelial somatic stem cells may be a commercially available cell population, or a cell population obtained from a living organism. For example, when human hepatic cells are used, the cells are prepared by separating commercially available frozen human hepatic cells produced by XenoTech, In Vitro Technologies, or the like, using a cell isolation kit, and further removing dead cells by centrifuge or the like. Further, it is also possible to use a hepatic cell population obtained by subjecting a liver tissue obtained from a living organism to collagenase digestion using a standard method, thereby separating the hepatic cells, and then removing dead cells. Similarly, epithelial somatic stem cells obtained from organs other than liver may also be obtained by a known method.

The cell population comprising epithelial somatic stem cells preferably has a high viability. For example, the viability is not less than 50%, more preferably not less than 60%, further preferably not less than 70%, further more preferably not less than 80%, particularly preferably not less than 90%. The viability of the cells may be measured using a commercially available analyzer. Further, the cell population comprising epithelial somatic stem cells preferably show high cell adhesion to a collagen-coated plate (e.g., not less than 70%).

The viability of the cell population comprising epithelial somatic stem cells can be measured using a known method. For example, the viability can be determined by treating a cell population comprising epithelial somatic stem cells with a trypan blue pigment, and measuring the proportion of the blue-stained dead cells with a microscope or the like.

(2) Protein Having an Activity for Causing Cells in G0 Phase or G1 Phase to Enter S Phase The "protein having an activity for causing cells in G0 phase or G1 phase to enter S phase" (in this specification, the protein may also be referred to as a "cell cycle reactivation protein") to be introduced into the cells as a gene is not limited insofar as the protein has an activity for causing cells in G0 phase or G1 phase to enter S phase.

The expression "causing cells in G0 phase or G1 phase to enter S phase" means an activity of (1) causing the quiescent cells in G0 phase, which have left (escaped) the cell cycle, to enter S phase, thereby causing the cells to reenter the cell cycle; or (2) acting on the cells in G1 phase, thereby shifting them to S phase.

The presence of the "activity for causing cells in G0 phase or G1 phase to enter S phase" may be confirmed by the following method.

Method for Confirming the Activity for Causing Cells in G0 Phase or G1 Phase to Enter S Phase The shift to S phase (DNA synthesis phase) may be confirmed by examining the activity of intake of 5-Bromo-2-deoxyuridine (BrdU), which is an analog of thymidine, into the cells. For example, BrdU is placed in a cell culture medium, and then reacted with a fluorescently-labeled anti-BrdU antibody, thereby immunostaining the cell surface; then, the activity is measured using a flow cytometer or the like.

Examples of the cell cycle reactivation proteins include proteins having an activity of promoting phosphorylation of Rb protein, such as cyclin-dependent kinase, cyclin, and the like. Examples of cyclin-dependent kinase include CDK1, CDK2, CDK3, CDK4, CDK6, and CDK7. Examples of cyclin include cyclin D. Among them, CDK4 and CDK6 are preferable, and CDK4 is more preferable.

For the cell cycle reactivating protein, a single gene, or a combination of two or more genes may be expressed.

The origin of the gene of the cell cycle reactivation protein is not particularly limited insofar as the effects of the present invention are ensured. The gene may be obtained from the same or different animal species as the cell population comprising epithelial somatic stem cells used in Step (A) is obtained from. The same animal species is more preferable.

The means for expressing the gene of the cell cycle reactivation protein is not limited insofar as the method is capable of expressing the cell cycle reactivation protein. For example, the gene may be subjected to transient expression or stable expression. Transient expression refers to a method of introducing a gene into cells by way of DNA transfection or the like, thereby transiently expressing the gene. A "transient period" generally means within several hours to several days. In contrast, stable expression refers to expression of a gene stably included in a chromosome. In order for the structures and properties of the epithelial somatic stem cells and epithelial differentiated cells that are produced by the method of the present invention being identical or very similar to the structures and properties of epithelial somatic stem cells or epithelial differentiated cells in vivo, it is preferable that the gene of the cell cycle reactivation protein is expressed transiently.

The transient expression is not particularly limited; however, it can be induced, for example, by introducing an expression vector having the target gene in a site downstream from the expression promoter, and expressing the gene from the expression vector. Examples of the expression promoter used in this method include, but are not limited to, CMV promoter, SV40 promoter, and the like. Further, examples of the expression vectors include, but are not limited to, nonviral vectors such as plasmid vectors or liposome; and virus vectors such as adenovirus vectors or retrovirus vectors. In view of safety of the resulting cells when the cells are used as a medicine, or in view of secure transient expression of the gene to be introduced, it is preferable to use a nonviral vector, in particular, a nonviral vector that does not include the replication origin of the host cell. To further ensure transient expression, it is possible to additionally perform a step of confirming that the cells are not incorporated in the chromosome. Accordingly, examples of suitable plasmid vectors include pcDNA and pSVL. The methods for introducing an expression vector into the cells include, but are not limited to, lipofection method, electroporation method, and a method of incorporating a gene into a viral vector to make the gene become infected with the virus.

The stable expression is not particularly limited. For example, the following methods can be used. An expression vector having the target gene and a dominant selective marker in a site downstream from the expression promoter is introduced into cells, thereby establishing a strain in which the target gene is incorporated in the chromosome. The gene is stably expressed in this strain. Examples of the expression promoter used in this method include, but are not limited to, CMV promoter, SV40 promoter, and the like. Examples of the dominant selective marker include, but are not limited to, various drug-resistant genes. When a drug-resistant gene is used as the dominant selective marker, it is possible to select only a cell strain that stably expresses the drug-resistant gene by continuously performing cell culture in the presence of the corresponding drug. In such a cell strain, the target gene is presumably also stably expressed. The stable expression of the target gene can be confirmed by analyzing the base sequence of the chromosome based on the DNA sequence or the like. Examples of the methods for introducing an expression vector into cells include, but are not limited to, lipofection method, and electroporation method. When a viral vector is used, a method of introducing a gene into a viral vector to make the gene become infected with the virus may be used.

When the gene is introduced into primary cultured cells, it is preferable to use a transfection reagent presumably having a relatively low cytotoxicity. In order to improve the transfection efficiency, for example, it is preferable to perform transfection using cells in a desirable condition. For human hepatic cells, cells within 2 to 3 days after the seeding on a culture plate have a relatively favorable cell condition.

Before performing Step (A), it is possible to culture a cell population comprising epithelial somatic stem cells in advance in a culture medium in which the original function of the cells can be maintained. For example, when a hepatic cell population is used as the cell population comprising epithelial somatic stem cells, a commercially available culture medium (Human Hepatocyte Serum-Free Medium, Toyobo Co., Ltd.) or the like suitable for the characteristic of the hepatic cells may be preferably used. When the frozen human hepatic cells are thawed and seeded on a plate, it is preferable to add about 5-10% of fetal bovine serum to promote cell adhesion.

The other culture conditions such as the culture temperature may be appropriately designed in view of desirable culture of individual epithelial somatic stem cells.

Step (A) is preferably performed while culturing the cells in a culture medium that supports the proliferation of the target epithelial somatic stem cells. An example of a suitable culture medium is a culture medium obtained by adding fetal bovine serum, human serum, or the like, to a DMEM (Dulbecco's modified Eagle's medium) culture medium (Gibco) or the like used for general mammal cell culture.

The culture medium used in Step (A) may further contain an extracellular growth factor. The extracellular growth factor is a substance having a function of externally supporting the proliferation of the target epithelial somatic stem cells. The extracellular growth factor is not particularly limited insofar as it has such a function. Examples of extracellular growth factor include cell growth factors, hormones for stimulating cell proliferation, and the like. Examples of cell growth factors include epithelial growth factor (EGF), hepatocyte growth factor (HGF), vascular endothelial growth factor (VEGF), fibroblast growth factor (FGF), and the like. Among them, EGF and HGF are preferable. Preferable examples of hormones include insulin. They may be used solely, or in a combination of two or more. For example, by combining at least one kind of cell growth factor selected from the group consisting of VEGF and FGF with at least one kind of cell growth factor selected from the group consisting of EGF and HGF, it is possible to additively or synergistically improve the proliferation. When the target epithelial somatic stem cells are hepatic stem cells, a hepatocyte growth factor (HGF) is preferably used.

The concentration of the extracellular growth factor to be added to the culture medium is not particularly limited. The concentration is preferably 0.1 to 200 ng/ml, more preferably 1.0 to 100 ng/ml, further preferably 5 to 50 ng/ml.

In addition to the DNA encoding a cell cycle reactivation protein, other genes may also be introduced and expressed in the epithelial somatic stem cells insofar as the proliferative ability and pluripotency of the epithelial somatic stem cells are not impaired. However, in view of the fact that the epithelial somatic stem cells proliferated in Step (B) have qualitative or structural properties identical or very similar to those of epithelial somatic stem cells in vivo, it is preferable that the epithelial somatic stem cells substantially do not contain exogenous DNA other than the DNA of the cell cycle-activating protein (for example, cyclin-dependent kinase). Similarly, for example, the gene to be introduced into the epithelial somatic stem cells, i.e., the gene related to cell cycle adjustment, is preferably only a gene of a cell cycle-activating protein (for example, cyclin-dependent kinase, in particular, CDK4 or CDK6). In one embodiment of the present invention, the epithelial somatic stem cells proliferated by the present invention preferably do not contain a gene encoding a human telomerase reverse transcriptase.

2. Step (B)

Step (B) performs culture of the cells obtained in Step (A) in the presence of an extracellular growth factor.

Through Step (B), as described below, epithelial somatic stem cells are predominantly proliferated from a cell population comprising epithelial somatic stem cells. The cell cycle of the epithelial somatic stem cells proceeds from G0 phase or G1 phase to S phase, then M phase (mitotic phase), and then to G1 phase again by the cell cycle reactivation protein externally introduced in Step (A). At the same instant, the extracellular growth factor in the culture medium activates the cell cycle reactivation protein, thereby allowing the epithelial somatic stem cells to continuously proliferate. In contrast, in cells other than epithelial somatic stem cells, the above proliferative activation by the cell cycle reactivation protein does not occur, or only a non-continuous transient proliferation occurs. Consequently, epithelial somatic stem cells are predominantly proliferated from a cell population comprising epithelial somatic stem cells.

In Step (B), the cells with the gene of the cell cycle reactivation protein expressed in Step (A) are cultured in the presence of an extracellular growth factor. When the culture medium used in Step (A) originally includes an appropriate extracellular growth factor, it is not necessary to exchange the culture medium when the cells with the expressed gene of the cell cycle reactivation protein are cultured. Further, instead of exchanging a culture medium, the extracellular growth factor may be added to a culture medium. The culture medium may be exchanged for a culture medium containing the extracellular growth factor, or the extracellular growth factor may be added to the culture medium after the culture medium is exchanged for a medium that does not contain an extracellular growth factor.

For the extracellular growth factor used herein, the extracellular growth factors described in Step (A) may be used (for example, EGF, HGF, VEGF, or FGF). When the target epithelial somatic stem cells are hepatic stem cells, a hepatocyte growth factor (HGF) is preferably used.

The concentration of the extracellular growth factor to be added to the culture medium is not particularly limited. The concentration is preferably 0.1 to 200 ng/ml, more preferably 1.0 to 100 ng/ml, further preferably 5 to 50 ng/ml.

When a new culture medium is used in Step (B), for example, a culture medium obtained by adding a component that supports the proliferation of the target epithelial somatic stem cells to a DMEM (Dulbecco's modified Eagle's medium) culture medium (Gibco) or the like generally used for mammal cell culture may be used.

In Step (B), the culture medium may be exchanged at an appropriate interval. Although it is not limited, the culture medium may be exchanged at a frequency of every 2 or 3 days. The culture medium may be exchanged for a culture medium containing the same concentration of an extracellular growth factor, or may be exchanged for a culture medium containing a different concentration of an extracellular growth factor. The culture medium may be exchanged for a culture medium containing the same extracellular growth factor, or may be exchanged for a culture medium containing a different extracellular growth factor.

Other culture conditions including the temperature of the culture may be appropriately designed according to a known method, depending on the type of epithelial somatic stem cells to be used for the culture.

Step (A) and Step (B) may be performed once individually, or a set of Step (A) and Step (B) may be repeated several times. When a set of Step (A) and Step (B) is performed several times, it is preferable to perform a set of Step (A) and Step (B) 2 to 10 times, more preferably 3 to 8 times, further preferably 3 to 5 times. Such repetitive sets of Steps (A) and (B) are preferred when the gene encoding a cell cycle reactivation protein is transiently expressed. This is because the peak of the transient expression is about three days after the transfection; thus, the gene expression is preferably performed continuously for a certain period of time to render the epithelial somatic stem cells proliferative.

Step (A) and Step (B) may be sequentially performed in this order, or another step may be performed between Step (A) and Step (B).

Step (B), or repetitive sets of Steps (A) and (B), may be performed until a desired amount of epithelial somatic stem cells is obtained. For example, as in Example 2 and Example 8, the sets of Steps (A) and (B) are repeatedly performed preferably for about 20 to 60 days.

When Step (B) is performed only once, Step (B) is preferably continued, for example, until sufficient colony formation by the epithelial somatic stem cells is confirmed. Thereby, an epithelial somatic stem cell population may be more easily obtained. The termination point of Step (B) is preferably a time point where colony formation of epithelial somatic stem cells is confirmed with a microscope or by visual inspection, or where colony formation of epithelial somatic stem cells including 10 to 10000 cell populations is confirmed, more preferably, where colony formation of epithelial somatic stem cells including 100 to 1000 cell populations is confirmed. The cell division of different cells (cells other than epithelial somatic stem cells) originally contained in the cell population comprising epithelial somatic stem cells is terminated due to the cell division limit by the end of Step (B) at the latest. Most of the cells slough off; or, even if they survive, the form of the cells is greatly changed. Therefore, the different cells are easily distinguishable from the epithelial somatic stem cells that form the colonies. Thus, a highly pure epithelial somatic stem cell population can be obtained.

When a set of Steps (A) and (B) are repeatedly performed, it is preferable to perform the sets of Steps (A) and (B), for example, until sufficient colony formation of the epithelial somatic stem cells is confirmed, so as to more easily obtain the epithelial somatic stem cell population. The sets of Step (A) and Step (B) are preferably repeated until colony formation of epithelial somatic stem cells is confirmed with a microscope or by visual inspection; or until colony formation of epithelial somatic stem cells including 10 to 10000 cell populations is confirmed, more preferably, until colony formation of epithelial somatic stem cells including 100 to 1000 cell populations is confirmed. The colony is usually formed several weeks to 1 month after Step (B). The cell division of different cells (cells other than epithelial somatic stem cells) originally contained in the cell population comprising epithelial somatic stem cells is terminated due to the cell division limit by the end of the final round of Step (B) at the latest. Most of the cells slough off; or, even if they survive, the form of the cells is greatly changed. Therefore, the different cells are easily distinguishable from the epithelial somatic stem cells forming the colonies. Thus, a highly pure epithelial somatic stem cell population can be obtained. Further, in this method, each round of Step (B) can be continued as long as the cells continue proliferating. It is also possible to stop Step (B) during the cell proliferation.

As described above, by performing Step (B), the epithelial somatic stem cells form colonies with their superior proliferation ability among a cell population comprising epithelial somatic stem cells. For other cells, the cell division is terminated by the end of Step (B) due to the cell division limit. Most of the cells slough off; or, even if they survive, the form of the cells is greatly changed from the original form. Therefore, these cells are easily distinguishable from epithelial somatic stem cells forming colonies. Accordingly, by collecting the colonies, the epithelial somatic stem cell population may be isolated as clones.

3. Miscellaneous

By performing a step of collecting the colonies after Step (B), epithelial somatic stem cells may be obtained. The collection of the colonies may be performed according to a known method. Any known method can be used, including a limiting dilution method, or a method using a micropipette with a microscope.

For example, when a hepatic cell population is used as a cell population comprising epithelial somatic stem cells, they are mostly hepatic parenchymal cells; however, non-parenchymal cells such as sinusoidal endothelial cells, stellate cells, Kupffer cells, and the like, are also included. The method of the present invention enables easy and efficient isolation of a very small amount of hepatic stem cells from such a mixed cell population containing various cells.

The production method of the present invention enables production of an epithelial somatic stem cell population containing epithelial somatic stem cells in an amount of preferably not less than 50%, more preferably not less than 80% (based on cell number). Further preferably, the production method of the present invention enables production of an epithelial somatic stem cell population substantially consisting only of epithelial somatic stem cells; further more preferably, an isolated epithelial somatic stem cell population.

In the present invention, the epithelial somatic stem cells are determined by whether the resulting cells are able to differentiate into target cells; however, the epithelial somatic stem cells are not limited thereto. Further, in the present invention, the epithelial somatic stem cells may also be determined by confirming the existence of a cell surface marker. For human hepatic cells, epithelial somatic stem cells can be determined by the following method; however, the method is not limited thereto.

It is possible to determine that the cells obtained from a cell population containing hepatic cells are hepatic stem cells when the cells are AFP positive, albumin negative, C-Met positive, EpCAM positive, Dlk positive, Thy1 positive, CK19 positive, and CD34 negative.

It is also possible to determine that the cells obtained from a cell population containing hepatic cells are human hepatic cells when the cells are AFP negative, albumin negative, C-Met positive, EpCAM positive, Dlk positive, Thy1 positive, CK19 positive, and CD34 negative.

The differentiation of hepatic stem cells into hepatic cells can be confirmed by the expression of a marker gene, for example, by a change to albumin and/or CYP (drug-metabolizing enzyme) positive.

Further, it is possible to determine that the cells obtained from a cell population containing epidermal cells are epidermal stem cells when the cells are β1 integrin positive and Dsg3 negative.

It is possible to determine that the cells obtained from a cell population containing intestinal epithelial cells are intestinal epithelial stem cells when the cells are Lgr5 positive, β-catenin positive, musashi-1 positive, c-kit negative, and Sca-1 negative.

The epithelial somatic stem cells obtained by the method of the present invention have properties that are the same or very similar to those of epithelial somatic stem cells in vivo. Thus, the epithelial somatic stem cells obtained by the method of the present invention are conducive to stable supply of highly pure epithelial differentiated cell populations. The thus-obtained epithelial differentiated cells are ultimately applicable to clinical usages such as cell preparation; or various research and development such as new drug development or disease research.

B. Production Method for Epithelial Differentiated Cells

The production method for epithelial differentiated cells includes a step of differentiating the epithelial somatic stem cells produced by the above-described production method of the present invention.

The differentiation step performs culture of epithelial somatic stem cells in a culture medium suitable for differentiation. The culture medium suitable for differentiation and other culture conditions are appropriately designed according to known conditions depending on the type of epithelial somatic stem cells and the target differentiated cells. For example, when hepatic stem cells are used as epithelial somatic stem cells to be differentiated into hepatic cells (hepatic parenchymal cell), the hepatic stem cells may be cultured in a serum-free culture medium (serum concentration=0 to 2%) that also does not contain an extracellular growth factor (for example, the concentration of EGF is 0 to 5 ng/ml). Appropriate culture conditions may be more specifically designed by a person skilled in the art by referring to the later-described Examples.

The formulation and conditions of the culture medium used for the differentiation into the target differentiated cells are not limited to the above examples; however, the culture is preferably performed substantially in the absence of blood serum (for example, human serum or bovine serum). This is because the differentiation of the epithelial somatic stem cells is suppressed in the presence of blood serum. Further, in secondary view of safety of differentiated cells for use in cell implants or medications, it is preferable to induce the differentiation of the cells under a serum-free condition. "Substantially serum-free condition" refers to a condition in which the volume concentration of blood serum in the culture medium is not more than 2%, preferably not more than 1%, more preferably not more than 0.5%. Further preferably, the culture medium is completely free of blood serum.

Further, when epithelial somatic stem cells are differentiated, it is preferable to culture the cells substantially in the absence of specific cell growth factors. This is because the differentiation of the epithelial somatic stem cells is suppressed in the presence of specific cell growth factors. More specifically, when epithelial somatic stem cells are differentiated, it is preferable to culture the cells substantially in the absence of epithelial growth factor (EGF) or liver cell growth factor (LCG), more preferably in the absence of both EGF and LCG. For example, the culture is preferably performed with no more than 5 ng/ml of EGF; more preferably, in the complete absence of EGF.

The culture of epithelial somatic stem cells may be a two-dimensional culture, or a three-dimensional culture. However, in view of rapid induction of differentiation, a three-dimensional culture is preferable. Three-dimensional culture literally refers to a cell culture that is performed three-dimensionally. Various materials for three-dimensional culture are already known. For example, it is possible to use collagen gel or permeable membranes.

The duration of hollow fiber cell culture or the like is, for example, 3 to 60 days, preferably 5 to 14 days; however, the duration of culture is not particularly limited.

When epithelial somatic stem cells are differentiated, the epithelial somatic stem cells are preferably cultured in advance for a predetermined period (priming culture) so as to activate the cells in the presence of an activation substance before the cells are cultured in a culture medium suitable for differentiation. The priming culture serves to advance the differentiation to the first stage. Thus, by performing the priming culture, it is possible to reduce the culture period of the subsequent culture for differentiation. For example, BMP or FGF is effective for the priming culture. As described above, the applications of ultimately obtained epithelial differentiated cells include clinical usages such as cell preparation; or various research and development, such as new drug development or disease research.

An application example of epithelial differentiated cells is shown below. By using a hepatic cell population prepared from a portion of a normal liver tissue obtained from a patient having a liver disease as a "cell population comprising epithelial somatic stem cells" in the present invention, hepatic stem cells can be obtained. After the hepatic stem cells are proliferated, the cells are implanted to the liver of the patient again by way of portal vein injection or the like. Thereby, it is possible to perform implant treatment without the risk of immunological rejection. Alternatively, the cells may be implanted into the liver of the patient after the obtained hepatic stem cells are proliferated and then further differentiated into normal hepatic cells.

C. Pharmaceutical Composition

By using the above epithelial somatic stem cells, or epithelial differentiated cells obtained from the epithelial somatic stem cells as an active ingredient, it is possible to produce a pharmaceutical composition (cell preparation). The cell preparation of the present invention may contain plural kinds of epithelial somatic stem cells or plural kinds of epithelial differentiated cells. The cell preparation of the present invention may contain both the epithelial somatic stem cells and the epithelial differentiated cells.

By administering an effective dose of the pharmaceutical composition of the present invention to a patient, it is possible to treat a disease. The diseases treatable by the pharmaceutical composition of the present invention are not particularly limited. Examples of the diseases include cancers, cardiovascular diseases, metabolic diseases, liver diseases, diabetes, hepatitis, hemophilia, neurodegenerative diseases, traumatic neurosis, autoimmune diseases, genetic defects, connective tissue diseases, anemia, infections, and transplant rejection.

The pharmaceutical composition of the present invention is administered through catheter administration, systemic injection, parenteral administration, or local injection such as intrauterine injection into embryo. The administration may be performed with a pharmaceutically acceptable substrate. The pharmaceutically acceptable substrate may be a biodegradable substrate.

The cell preparation of the present invention may be a preparation in which an exogenous gene is introduced. The introduction of the exogenous gene into the epithelial somatic stem cells or epithelial differentiated cells produced by the method of the present invention may be performed using known methods in the related technical fields. The exogenous gene to be introduced may be appropriately selected depending on the intended use (for example, gene therapy) of the cell preparation. Examples of the genes include a gene encoding a drug-metabolizing enzyme.

The method for administering the cell preparation of the present invention is appropriately selected depending on the affected part to which the preparation is applied. Examples of the dosage forms include intravenous injection, intraarterial injection, portal vein injection, intradermal injection, hypodermic injection, submucosal injection and intraperitoneal injection. In addition, the administration may also be performed by adhering a cell sheet resulting from a culture to the affected part. Alternatively, the administration may be performed by adhering or implanting a tissue-like cell, which is obtained by three-dimensional cell culture using a biocompatible scaffold, into the affected tissue.

The form of the cell preparation of the present invention is appropriately selected according to the administration method and the like. Examples of the preparation forms include liquid agents in which the cells are suspended, gel agents in which the cells are suspended, cell sheets, and tissue-like cell aggregates.

The administration amount and the administration frequency of the cell preparation of the present invention are appropriately determined according to the administration method, preparation form, condition of the patient, cell activity level, and the like. The single dose is not less than the effective amount. Further, the cell preparation of the present invention may be administered, for example, once a day, or about 2 or 3 times a day. It is also possible to administer, at one time, an amount corresponding to a 2-day dose or a 1-week dose.

The proportion of the epithelial somatic stem cells or epithelial differentiated cells in the cell preparation of the present invention is designed according to the administration method, preparation form, administration amount, administration frequency, and the like.

In addition to the active ingredient (epithelial somatic stem cells or epithelial differentiated cells), the cell preparation of the present invention may further contain other components. Examples of components include formulation components for the various preparation forms, preservation stabilizers for stable preservation, and other medicinal ingredients. Examples of other medicinal ingredients include anti-inflammatory agents, antimicrobial agents, immunosuppressants, cell growth factors, hormones, and the like.

C. Kit for Isolating Epithelial Somatic Stem Cells

A kit for isolating the epithelial somatic stem cells of the present invention is a kit for isolating epithelial somatic stem cells from a cell population comprising epithelial somatic stem cells. The kit includes an expression vector for expressing a cell cycle reactivation protein and an extracellular growth factor.

The epithelial somatic stem cells, the extracellular growth factor, the cell cycle reactivation protein, and the expression are the same as those in Item A above.

The same expression vector as the expression vector used in Item A may be used.

The kit may also include an appropriate extracellular growth factor described in Item A above.

D. Method for Producing Epithelial Somatic Stem Cells with Reactivated Cell Cycle The method for producing epithelial somatic stem cells with reactivated cell cycle of the present invention includes a step of expressing a gene of a cell cycle reactivation protein in epithelial somatic stem cells in the quiescent phase.

The epithelial somatic stem cells, the cell cycle reactivation protein, and the expression are the same as those described in Item A above.

The "epithelial somatic stem cells in the quiescent phase" refers to (i) quiescent epithelial somatic stem cells that have left the cell cycle and shifted to G0 phase from G1 phase, and (ii) epithelial somatic stem cells in G1 phase.

The "epithelial somatic stem cells with reactivated cell cycle" refers to epithelial somatic stem cells that reentered a cell cycle, i.e., that reentered S phase from (i) the quiescent state in which the cells have left the cell cycle and shifted to G0 phase from G1 phase, or from (ii) G1 phase. The reactivation of the cell cycle may be evaluated, for example, by measuring the entry of BrdU or labeled thymidine into the cell nucleus or phosphorylation of RB protein.

The present invention is more specifically explained below with reference to Examples and Test Examples. However, the present invention is not limited to these examples.

EXAMPLES

Example 1

Proliferation of Hepatic Cell Population by Introduction of CDK Gene (1) Culture of Primary Human Hepatic Cell Frozen primary human hepatic cells (XenoTech) were thawed, and then subjected to Ficoll separation using a hepatocyte isolation kit (XenoTech) to separate viable cells from dead cells, thus obtaining a hepatic cell suspension having a high viability. The cells were suspended in a human hepatocyte serum-free medium (Toyobo Co., Ltd.) containing fetal bovine serum at a proportion of 10%, and seeded on a collagen-coated 24-well cell culture plate (AGC Techno Glass Co., Ltd.) at a cell density of $1.1 \times 10^5$/well. The seeded cells were cultured in an incubator for an entire day and night at 37° C., 5% $CO_2$, so that the hepatic cells were fully adhered to the plate.

(2) Transfection

On the following day of the seeding of human hepatic cells, the cells were subjected to transfection using the following culture medium and gene. The transfection was performed using a commercially available protein expression plasmid pcDNA3 (Invitrogen). DNA encoding human CDK4 was inserted into a cloning site between EcoR I and Xba I. The DNA encoding human CDK4 was obtained through RT-PCR with primers created based on the base sequences (gene accession number: CAG47043) registered in NCBI (National Center for Biotechnology Information), and, as a template, total RNA purified from HuS-E/2 cell (cells obtained from human hepatic cells; deposited with International Patent Organism Depositary, National Institute of Advanced Industrial Science and Technology under accession No. FERM ABP-10908). The primers used above were a forward primer having the base sequence of SEQ ID NO: 1 and a reverse primer having the base sequence of SEQ ID NO: 2. The base sequence of SEQ ID NO: 1 includes a sequence corresponding to FLAG Tag.

The thus-obtained plasmid (pcDNA-FLAG-CDK4) of the DNA encoding human CDK4 in which a FLAG tag is introduced in the N-terminus of an open reading frame was added in an amount of 0.2 μg per well together with an Effectene transfection reagent (Qiagen), thereby introducing a gene into hepatic cells.

The transfection was performed once in every 3 to 5 days, 3 times in total, under the following four conditions.

Group 1: A culture medium obtained by adding 20 ng/ml of a hepatocyte growth factor (HGF) (human HGF, Toyobo Co., Ltd., Code: HGF-101, CHO cell recombinant) to a DMEM-based culture medium containing 5% fetal bovine serum and 5% human serum. The gene introduced was CDK4 (pcDNA-cdk4).

Group 2: The same culture medium as that of Group 1. The gene introduced was a plasmid (pcDNA) only.

Group 3: A DMEM-based culture medium containing 5% fetal bovine serum, 5% human serum. The gene introduced was CDK4 (pcDNA-cdk4).

Group 4: The same culture medium as that of Group 3. The gene introduced was a plasmid (pcDNA) only.

In FIG. 1, Group 1 is denoted by "CDK4+HGF," Group 2 is denoted by "pcDNA3+HGF," Group 3 is denoted by "CDK4," and Group 4 is denoted by "pcDNA3."

(3) Cell Number Measurement

On Day 1, Day 4, and Day 10 after the transfection, the number of the cells in each condition was measured (the cell number of 3 wells for each condition and each point). The measurement of cell number was performed using an XTT cell proliferation assay kit (Cosmo Bio Co., Ltd.).

As a result, as shown in FIG. 1, significant cell proliferation was observed only in Group 1 using CDK4 gene-introduced cells with a culture medium containing HGF. Three colonies were observed in the medium. The slight increase in cell number observed in Groups 2 to 4 is assumed to result from an increase of fibroblasts or the like. Hepatic cells are known as having little proliferative ability in vitro. However, it was confirmed that the proliferation of hepatic cells is possible by the method of the present invention. This indicates that the cell cycle of the proliferated cell group was changed.

Example 2

Acquisition of Human Hepatic Stem Cell [1]

(1) Culture of Primary Human Hepatic Cells

Frozen primary human hepatic cells (XenoTech) were thawed, and then subjected to Ficoll separation using a hepatocyte isolation kit (XenoTech) to separate viable cells from dead cells, thus obtaining a hepatic cell suspension having a high viability. The cells were suspended in a human hepatocyte serum-free medium (Toyobo Co., Ltd.) containing fetal bovine serum at a proportion of 10%, and seeded on a collagen-coated 12-well cell culture plate (AGC Techno Glass Co., Ltd.) at a cell density of $5 \times 10^5$/well. The seeded cells were cultured in an incubator for two days at 37° C., 5% $CO_2$, so that the hepatic cells were fully adhered to the plate.

(2) Transfection

On Day 3 after the seeding of human hepatic cells, the culture medium was exchanged for a DMEM-based culture medium containing 5% fetal bovine serum, 5% human serum and 10 ng/ml HGF. The transfection was performed using a commercially available protein expression plasmid pcDNA3 (Invitrogen). A human CDK4 gene or human CDK6 gene was inserted into a cloning site between EcoRI and XbaI or a cloning site between Hind III and BamHI of the plasmid. The human CDK4 gene or human CDK6 gene was obtained through RT-PCR with primers created based on the base sequences (gene accession number of human CDK6 gene: NP 001138778) registered in NCBI (National Center for Biotechnology Information), and, as a template, total RNA purified from HuS-E/2 cell. The primers for obtaining DNA encoding CDK4 were the same as those used in Example 1. The primers for obtaining DNA encoding CDK6 were a forward primer having the base sequence of SEQ ID NO: 3 and a reverse primer having the base sequence of SEQ ID NO: 4. The forward primer includes sequences corresponding to HindIII site and Flag Tag.

The thus-obtained plasmid (pcDNA-FLAG-CDK4 or pcDNA-FLAG-CDK6) of the DNA encoding human CDK4 or CDK6 in which a FLAG tag in introduced in the N-terminus of an open reading frame was added in an amount of 0.3 μg per well together with an Effectene transfection reagent (Qiagen), thereby introducing a gene into hepatic cells. Thereafter, transfection was performed once in every 5 days, 5 times in total. As a negative control, another transfection of hepatic cells was performed in the same manner in a different well using a plasmid that does not contain a CDK gene.

(3) Separation of Cell Clone

On Day 35 of the culture, the cells transfected as a negative control all sloughed off, and none remained. At this point, formation of several colonies was observed in the pcDNA-FLAG-CDK4-transfected cells. Similarly, formation of several colonies was also observed in the pcDNA-FLAG-CDK6-transfected cells. These colonies were cloned using a limiting dilution method, thereby obtaining clonal cells. The clones thus obtained were named HYM cells. In HYM cells, continuous proliferation for 1 year or more after the establishment was confirmed, and thereby a self-replication ability was confirmed.

(4) Expression of Differentiation Marker

Each of the obtained HYM cell clones was examined mainly with hepatic cell-related differentiation markers. More specifically, cells of albumin, AFP, CD34, Thy-1 (CD90), c-Met, EpCAM, Dlk, c-kit, and CK19 were collected, and RT-PCR was performed using the extracted RNA to examine mRNA expression. FIG. 2 shows the results.

These cells exhibited common cell surface marker characteristics: albumin negative, c-Met positive, EpCAM positive, Dlk positive, Thy1 positive, and CD34 negative. Further, most of them were CK19 positive, although some had very weak positive (+/−). As such, all HYM cell strains presented a cell surface marker characteristic specific to hepatic stem cells. Hence, it was confirmed that these cells were all undifferentiated hepatic stem cells. The results clearly showed that the method of the present invention enables acquisition of isolated undifferentiated hepatic stem cells capable of self-replication (i.e., proliferation).

Example 3

Induction of Differentiation into Hepatic Cells 1

HYM cells (hepatic stem cell clone) were cultured in a collagen-coated 12-well plate containing 0.5% human serum and 0.5% fetal bovine serum. When the cells were proliferated to the subconfluent level, the medium was exchanged for a serum free culture medium (human hepatic cell serum-free culture medium, Toyobo Co., Ltd., Code: TMHHM-001) and the culture was continued to induce differentiation. After the medium was exchanged for a serum-free culture medium, the culture medium was exchanged at a frequency of 2 or 3 days, and the culture was continued for 2 months. After 1 month and 2 months of the culture, the hepatic cell function, i.e., albumin production, and mRNA expression of the drug-metabolizing enzyme were examined. The results showed that the mRNA expression amount was increased in albumin and drug-metabolizing enzyme markers other than CYP2E1 (FIG. 3). The results showed that the hepatic stem cells were differentiated into hepatic cells; and that therefore, the established HYM cells are capable of differentiation.

Example 4

Induction of Differentiation into Hepatic Cells 2
(Comparison Between Two-Dimensional Culture and
Three-Dimensional Culture)

FIG. 4 shows an experiment procedure of the present Example. The HYM cells obtained in Example 2 were cultured in a culture medium obtained by adding FGF4 (30 ng/ml) and BMP2 (20 ng/ml) to a hepatocyte basal medium (Lonza) for 5 days (priming culture). The cells were collected thereafter, and a part of the cells was seeded on a collagen-coated 12-well plate and cultured in a human hepatic cell serum-free culture medium (Toyobo Co., Ltd., Code: TMHHM-001) (two-dimensional culture). FGF4 and BMP2 were obtained from PeproTech.

In the same manner, another part of the isolated cells was collected five days after the priming culture, and cultured in Mebiol Gel (Ikeda Scientific Co., Ltd., Code: PMW20-1005) using a human hepatic cell serum-free culture medium (Toyobo Co., Ltd., Code: TMHHM-001) (three-dimensional culture).

On Day 0, Day 5, Day 15, Day 25, and Day 35 of the priming culture, the cells were collected from the HYM cells subjected to the two-dimensional culture, and RNA was extracted to examine the expression of genes of albumin (ALB), AFP, CK19, Dlk, EpCAM, Cxcr4, and Sox17. For the HYM cells subjected to the three-dimensional culture, the cells were collected on Day 25 and Day 35 of the three-dimensional culture, and RNA was extracted to examine the expression of the same genes.

The results showed that the cells of the two-dimensional culture were slightly albumin positive on Day 25, and strongly albumin positive on Day 35, thus presenting its differentiation into hepatic cells. In contrast, in the three-dimensional culture, the cells were changed to strongly albumin positive on Day 25, thus showing that the cells were more rapidly differentiated into hepatic cells than the cells in the two-dimensional culture. Further, in the three-dimensional culture, the AFP expression as an undifferentiated endoderm marker disappeared, indicating enhanced differentiation (FIG. 5). Moreover, the expression of Dlk gene as a hepatic stem cell marker also disappeared with time both in the two-dimensional culture and the three-dimensional culture, indicating that the differentiation from the hepatic cells into hepatic stem cells was induced by the two-dimensional culture and the three-dimensional culture. Since the disappearance was faster in the three-dimensional culture than in the two-dimensional culture, it was revealed that the differentiation can be further promoted by using the three-dimensional culture.

Example 5

Induction of Differentiation Into Bile Duct Epithelial
Cell (Comparison between Two-Dimensional
Culture And Three-Dimensional Culture)

FIG. 6 shows an experiment procedure of Example 5. First, the HYM cells obtained in Example 2 were cultured in a bile duct epithelial cell differentiation induction culture medium obtained by adding nicotinamide (10 mM), HEPES (20 mM), $NaHCO_3$ (17 mM), pyruvate (550 mg/L), ascorbic acid-2-phosphate (0.2 mM), glucose (14 mM), glutamine (2 mM), dexamethasone (100 nM), insulin (6.25 ug/ml), transferrin (6.25 ug/ml), selenious acid (6.25 ng/ml), bovine serum albumin (1.25 mg/ml), linoleic acid (5.35 ug/ml), and fetal bovine serum (5%) to a DMEM culture medium for 7 days (priming culture). The cells were collected thereafter, and a portion of the cells was seeded on a collagen-coated 12-well plate and cultured again using a bile duct epithelial cell differentiation induction culture medium (two-dimensional culture).

In the same manner, a portion of the cells isolated seven days after the priming culture was seeded on a 12-well plate, and cultured in collagen and Matrigel (Becton, Dickinson and Company). The resulting cells were cultured using a bile duct epithelial cell differentiation induction culture medium (three-dimensional culture).

On Day 0, Day 7, Day 17, Day 27, and Day 37 of the priming culture, the cells were collected from the HYM cells subjected to the two-dimensional culture, and RNA was extracted to examine the expression of genes of albumin (ALB), AFP, CK19, Dlk, and EpCAM. For the HYM cells subjected to the three-dimensional culture, the cells were collected on Day 20 and Day 30 of the three-dimensional culture, and RNA was extracted to examine the expression of the same genes.

Figure 7:
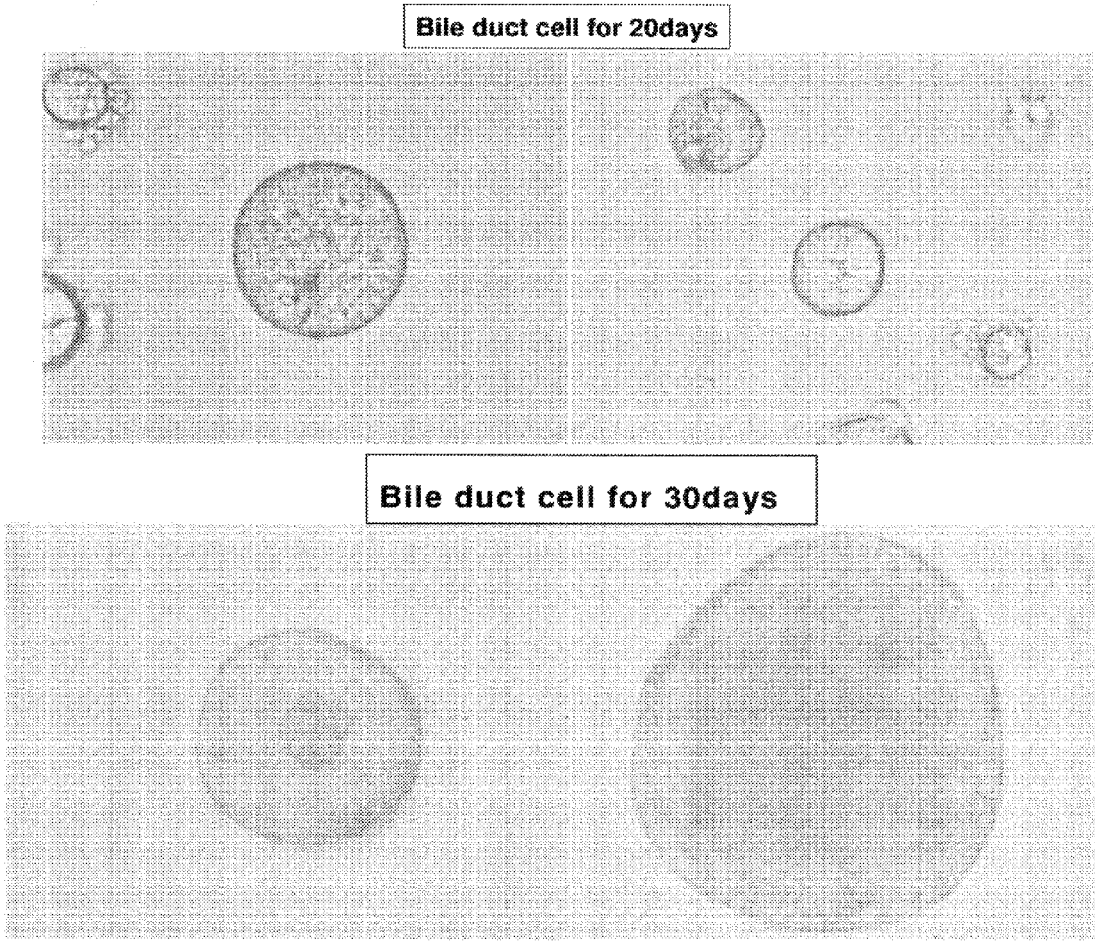
FIG. 7 shows changes in cell form due to induction of differentiation of HYM cells in Example 5. The upper figure shows a form on Day 20 of three-dimensional culture, and the lower figure shows a form on Day 30 of three-dimensional culture.

According to the results, although no significant change was observed in the two-dimensional culture, a significant change in the cell form was observed in the three-dimensional culture. FIG. 7 shows the states on Day 20 and Day 30 of the three-dimensional culture. As shown in the figure, a plurality of cells are aligned with a specific orientation, forming a spherical (left) or tubular (right) structure (cyst). The cells forming such a three-dimensional structure have a polarity such that the inner portion and the outer portion of the structure have different properties. Bile duct epithelium is known to have such a polar structure during the formation of a bile duct.

Figure 8:
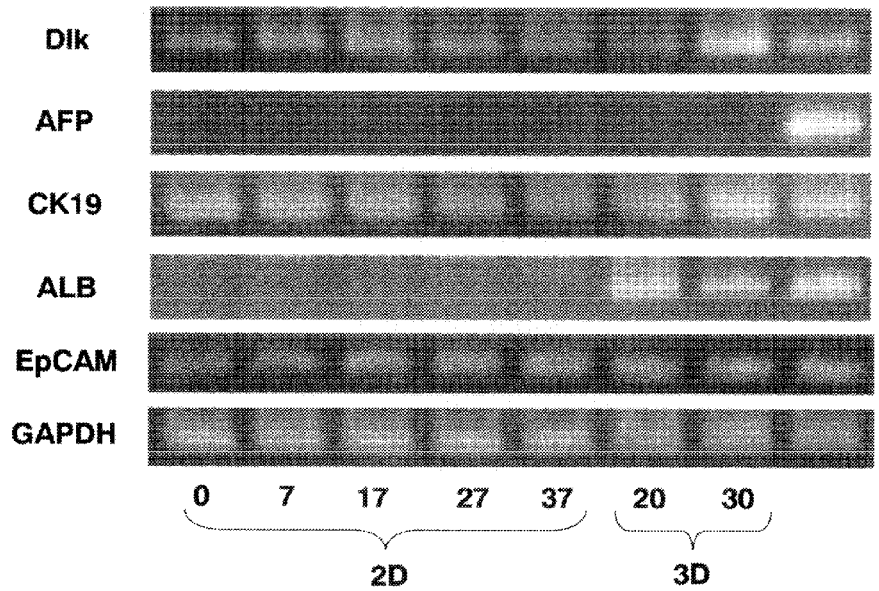
FIG. 8 shows changes in expression of differentiation marker genes due to differentiation induction of HYM cells in Example 5. The numbers in the horizontal axis denote the number of days after the priming culture.

Further, in the cell population subjected to the three-dimensional culture, the expression of CK19 gene as a bile duct epithelial marker was strongly induced after 30 days; at the same time, a decrease in ALB gene expression was also observed (FIG. 8). This shows that the differentiation of HYM cells into bile duct epithelial cells was induced.

The results of the present Example and Example 5 revealed that the HYM cells are capable of differentiation into hepatic cells and bile duct epithelial cells. Accordingly, it was confirmed that the cells obtained by the production method of the present invention are pluripotent hepatic stem cells.

Example 6

Induction of Differentiation into Hepatic Cells 3 (Differentiation Induction by Proliferation Suppression)

Figure 9:
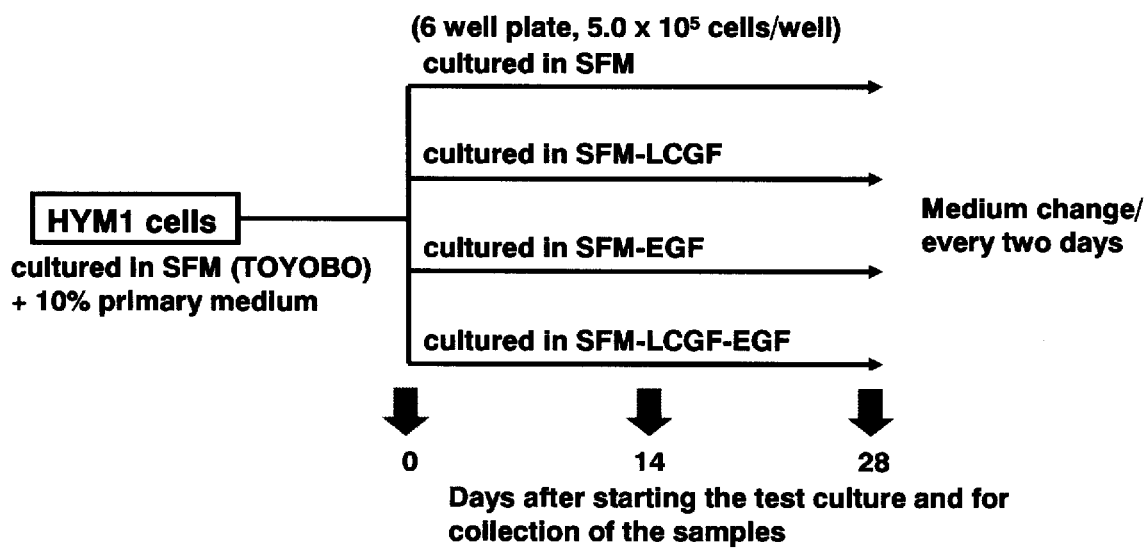
FIG. 9 shows the procedure of an experiment of differentiation induction of HYM cells in Example 6.
Figure 10:
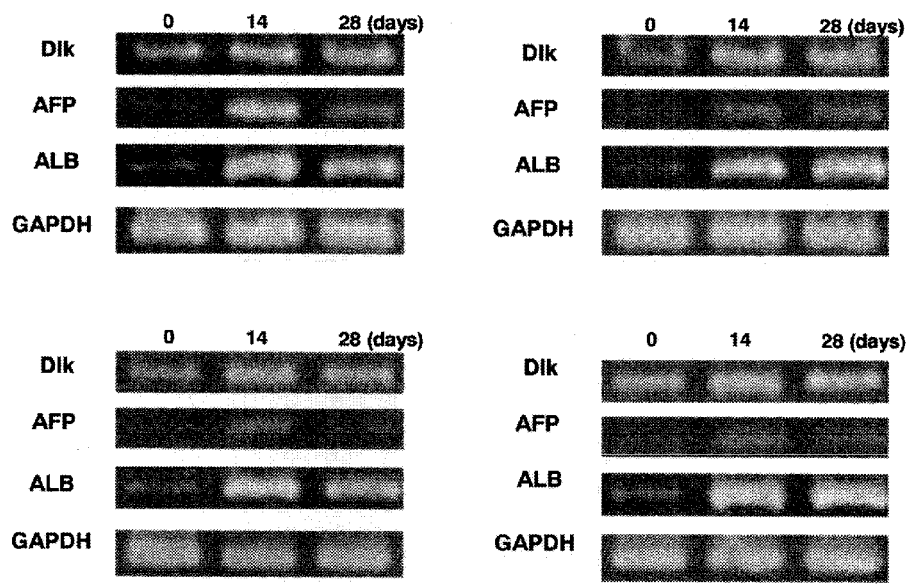
FIG. 10 shows changes in expression of differentiation marker genes with time due to induction of differentiation of HYM cells using a growth factor-deficient serum-free culture medium in Example 6. The upper-left diagram shows the results of culture using a hepatic cell serum-free culture medium containing EGF. The upper-right diagram shows the results of culture using a hepatic cell serum-free culture medium that does not contain EGF. The lower-left diagram shows the results of culture using a hepatic cell serum-free culture medium that does not contain LCGF. The lower-right diagram shows the results of culture using a hepatic cell serum-free culture medium that does not contain EGF and LCGF.

FIG. 9 shows an experiment procedure of Example 6. In the present Example, differentiation into hepatic cells was induced using a medium that does not contain a cell growth factor. The HYM cells were cultured in a mixed medium containing 9 volume of human hepatic cell serum-free culture medium (Serum-Free Medium: SFM) (Toyobo Co., Ltd., Code: TMHHM-001) and 1 volume of DMEM-based culture medium containing 5% fetal bovine serum, 5% human serum, and 20 ng/ml HGF for 7 days (priming culture). In the present Example, the resulting cells were then cultured in the following four different differentiation induction culture media for a comparison of the differentiation induction effect.
First culture medium: Human hepatic cell serum-free culture medium containing EGF
Second culture medium: Human hepatic cell serum-free culture medium that does not contain LCGF (Liver Cell Growth Factor)
Third culture medium: Human hepatic cell serum-free culture medium that does not contain EGF
Fourth culture medium: Human hepatic cell serum-free culture medium that does not contain LCGF or EGF On Day 0, Day 14, and Day 28 of the culture using a differentiation induction culture medium, the cells were collected, and RNA was extracted to examine the expression of genes of albumin (ALB), AFP, and Dlk. The results showed that, in particular, the cells cultured in a human hepatic cell serum-free culture medium that does not contain LCGF or EGF exhibited a significant effect due to the removal of growth factor. In this culture, the AFP expression appeared once was decreased on Day 28, while strong ALB expression was continuously observed from Day 14 through Day 28 (FIG. 10).

Figure 11:
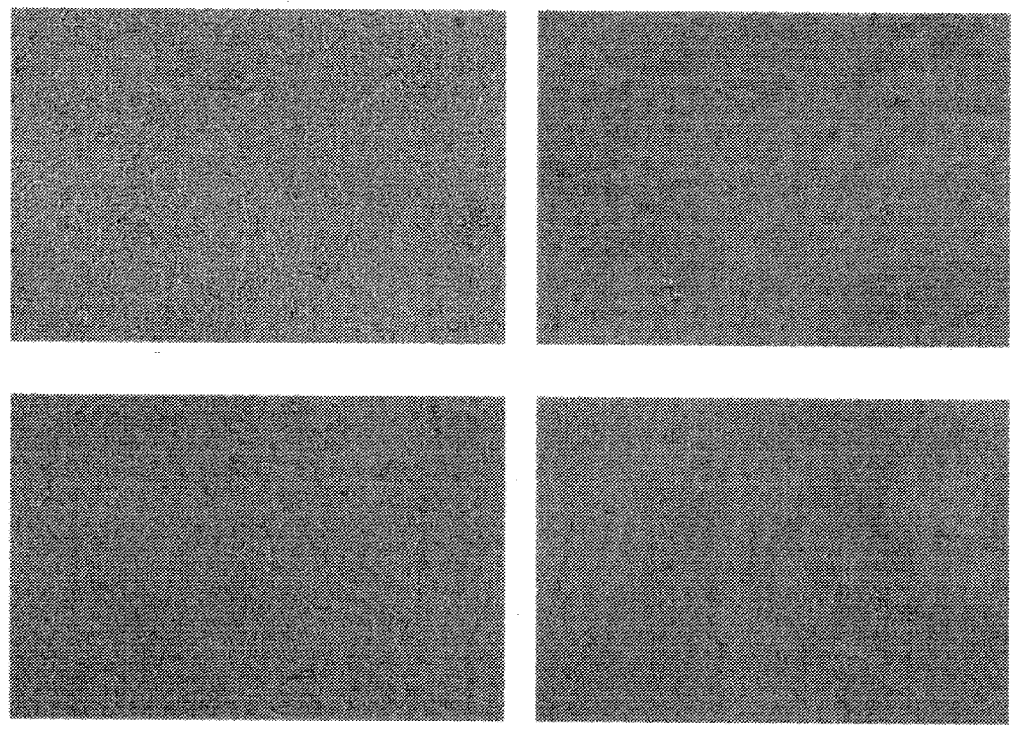
FIG. 11 is an image showing changes in cell form due to induction of differentiation of HYM cells using a growth factor-deficient serum-free culture medium in Example 6. The upper-left image shows the results of culture using a hepatic cell serum-free culture medium containing EGF. The upper-right image shows the results of culture using a hepatic cell serum-free culture medium that does not contain EGF. The lower-left image shows the results of culture using a hepatic cell serum-free culture medium that does not contain LCGF. The lower-right image shows the results of culture using a hepatic cell serum-free culture medium that does not contain EGF and LCGF.

Further, whereas a significant change in the cell form was not observed in the human hepatic cell serum-free culture medium containing EGF, the HYM cells in the human hepatic cell serum-free culture medium that does not contain EGF had a form similar to the cobblestone-like primary cultured hepatic cells four days after the culture. Further, a part of the cells had a structure similar to a bile duct epithelium (FIG. 11). The results showed that the differentiation of the HYM cells into hepatic cells can be promoted by using a culture medium that does not contain a cell growth factor.

Example 7

Induction of Differentiation into Hepatic Cells 4 (Induction of Differentiation by Proliferation Suppression of Fluorescent Protein-Introduced HYM Cells)

Figure 12:
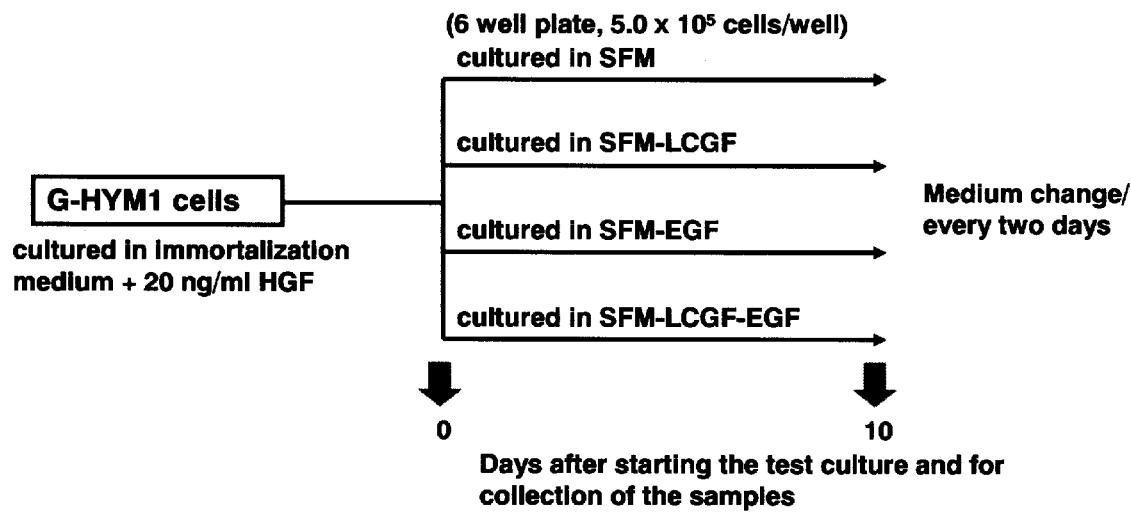
FIG. 12 shows the procedure of an experiment of differentiation induction of HYM cells in Example 7.

FIG. 12 shows an experiment procedure of Example 7. In the present Example, a fluorescent protein (GFP) gene was introduced into HYM cells, thereby producing GFP-expression HYM cells (hereinafter referred to as G-HYM). Then, with a culture medium from which a cell growth factor is removed by the same scheme as in Example 6, the induction of differentiation into hepatic cells was conducted.

G-HYM cells were produced in the following manner. An enhanced GFP gene inserted into a plasmid was introduced into HYM cells by transfection according to a standard method. The transfection was performed using a commercially available protein expression plasmid pcDNA3 (Invitrogen), and an enhanced GFP gene was inserted into a cloning site. This plasmid (pcDNA3-EGFP) was added to a culture medium containing HYM cells together with an Effectene transfection reagent (Qiagen), thereby introducing a gene into HYM cells (pcDNA3-EGFP). After introducing the gene, clones having a high GFP expression and a strong proliferative ability were selected from the cell colony proliferated in the culture medium containing G418, thereby obtaining G-HYM clones.

The G-HYM cells thus obtained were cultured for 7 days in a DMEM-based culture medium containing 5% fetal bovine serum, 5% human serum, and 20 ng/ml HGF (priming culture); thereafter, the cells were cultured in a human hepatic cell serum-free culture medium that did not contain EGF.

Figure 13:
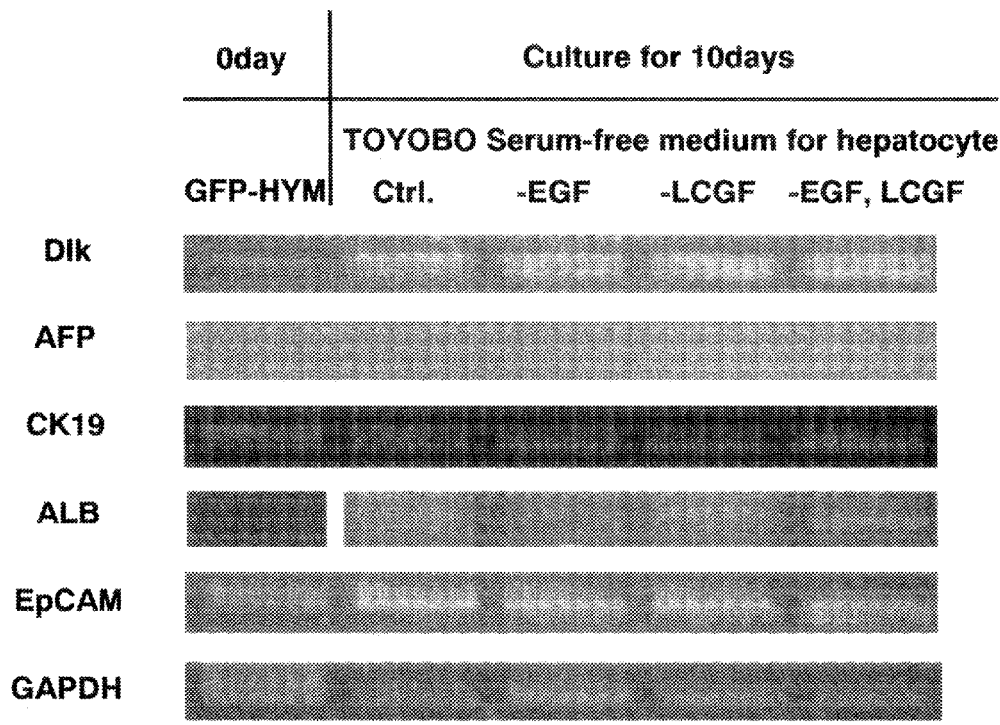
FIG. 13 shows changes in expression of differentiation marker genes due to induction of differentiation of G-HYM cells using a growth factor-deficient serum-free culture medium in Example 7.

The cells were isolated ten days after the culture, and RNA was extracted to examine the expression of genes of albumin (ALB), AFP, and Dlk, with the result that ALB was turned to positive (FIG. 13). Further, as in the G-HYM cell differentiation in Example 6, all of the HYM cells showed a form similar to the flagstone-like primary cultured hepatic cells. Further, a part of the cells had a structure similar to a bile duct epithelium (FIG. 14).

The results of Examples 3 to 7 showed that the HYM cells are capable of differentiation into both bile duct epithelial cells and hepatic cells. Further, it was observed that the proliferation of HYM cells was continued over a long period from the establishment of the cells. These results also showed that HYM cells are hepatic stem cells.

Further, as described in Example 7, it was shown that the HYM cells can be differentiated after introduction of a desired gene. This indicates that, for example, it is possible to introduce a gene encoding a peptide effective for liver disease treatment into HYM cells (more specifically, the hepatic stem cells produced by the method of the present invention are useful for gene therapy).

Example 8

Acquisition of Human Hepatic Stem Cell [2]

To verify the universality of the technique of the present invention, the same experiment as in Example 2 was conducted using primary human hepatic cells obtained from a donor different from that of the primary human hepatic cells used in Example 2.
(1) Culture of Primary Human Hepatic Cell
Frozen primary human hepatic cells (Gibco) were thawed, and a hepatic cell suspension was prepared by suspending the cells in a human hepatocyte serum free medium (Toyobo Co., Ltd.) containing 10% fetal bovine serum. The cells were seeded on a collagen-coated 12-well cell culture plate (AGC Techno Glass Co., Ltd.) at a cell density of $5 \times 10^5$/well. The seeded cells were cultured in an incubator for 2 days at 37° C., 5% $CO_2$, so that the hepatic cells were fully adhered to the plate.

(2) Transfection

On Day 2 of the seeding of human hepatic cells, the culture medium was exchanged for a DMEM-based culture medium containing 5% fetal bovine serum, 5% human serum, and 10 ng/ml HGF. The transfection was performed using a commercially available protein expression plasmid pcDNA3 (Invitrogen). The human CDK4 gene was inserted into a cloning site between EcoR I and Xba I. The plasmid (pcDNA-FLAG-CDK4) of the DNA encoding CDK in which a FLAG tag is introduced in the N-terminus of an open reading frame obtained above was added to a culture medium in an amount of 0.3 µg/well together with an Effectene transfection reagent (Qiagen), thereby introducing CDK4 gene into a hepatic cell population. Thereafter, the transfection was performed once in every 2 days, 5 times in total. As a negative control, another transfection of hepatic cells was performed in the same manner in a different well using a plasmid that does not contain CDK gene.

(3) Separation of Cell Clone

On Day 45 of the culture, the cells transfected as a negative control all sloughed off, and none remained. At this time, formation of six colonies was observed in the pcDNA-FLAG-CDK4-transfected cells. These colonies were cloned using a limiting dilution method, thereby obtaining clonal cells (HYM cells). In these cells, continuous and stable proliferation such as that of the clones in Example 2 was confirmed, and thereby a self-replication ability was confirmed.

(4) Expression of Differentiation Marker

The resulting HYM cell clones were examined with hepatic cell-related differentiation markers. More specifically, cells of albumin, AFP, CD34, Thy-1 (CD90), c-Met, EpCAM, Dlk, c-kit, and CK19 were collected; and RT-PCR was performed using total RNA extracted from the collected cells to examine the expression of mRNA. FIG. 15 shows the results.

As in the HYM cells obtained in Example 2, these cells exhibited common cell surface marker characteristics: albumin negative, c-Met positive, EpCAM positive, Dlk positive, Thy1 positive, CK19 positive, and CD34 negative. As such, it was confirmed that the undifferentiated hepatic stem cells (HYM cells) can be obtained by the method of the present invention, even when the hepatic cells are obtained from a different donor.

The invention claimed is:
1. A method for producing an epithelial somatic stem cell, comprising:
 (A) expressing a gene of a protein having an activity for causing a cell in G0 phase or G1 phase to enter S phase, in a cell population comprising an epithelial somatic stem cell; and
 (B) culturing the cell obtained in the Step (A) in the presence of an extracellular growth factor,
 wherein the protein is a cyclin-dependent kinase, and
 wherein the cell population is a hepatic cell population.

2. The method according to claim 1, wherein the expression is transient expression.

3. The method according to claim 1, wherein Step (A) and Step (B) are repeated at least twice.

4. The method according to claim 1, wherein the protein is at least one protein selected from the group consisting of cyclin-dependent kinase 4 and cyclin-dependent kinase 6.

5. The method according to claim 1, wherein the cell population is a primary-cultured somatic cell population.

6. The method according to claim 1, wherein the extracellular growth factor is a hepatocyte growth factor (HGF).

7. The method according to claim 1, wherein the protein is at least one protein selected from the group consisting of cyclin-dependent kinase 1, cyclin-dependent kinase 2, cyclin-dependent kinase 3, cyclin-dependent kinase 4, cyclin-dependent kinase 6, and cyclin-dependent kinase 7.

* * * * *